(12) United States Patent
Sulc et al.

(10) Patent No.: US 11,562,330 B1
(45) Date of Patent: Jan. 24, 2023

(54) REMOTE CARE SYSTEM

(71) Applicant: EAM Tech Solutions, LLC, Aurora, OH (US)

(72) Inventors: Linda M. Sulc, Aurora, OH (US); Steven J. Sulc, Chagrin Falls, OH (US); Jennifer L. Sulc, Cleveland, OH (US); Megan C. Sulc, Chagrin Falls, OH (US); Brett M. Tevepaugh, Chagrin Falls, OH (US); Christopher A. Zellner, Cleveland, OH (US)

(73) Assignee: EAM Tech Solutions, LLC

( * ) Notice: Subject to any disclaimer, the term of this patent is extended or adjusted under 35 U.S.C. 154(b) by 676 days.

(21) Appl. No.: 16/553,332

(22) Filed: Aug. 28, 2019

Related U.S. Application Data

(60) Provisional application No. 62/724,845, filed on Aug. 30, 2018.

(51) Int. Cl.
| | |
|---|---|
| *G06Q 10/10* | (2012.01) |
| *G06Q 10/06* | (2012.01) |
| *G06F 16/438* | (2019.01) |
| *G10L 25/48* | (2013.01) |
| *G16H 40/20* | (2018.01) |

(52) U.S. Cl.
CPC ....... *G06Q 10/1093* (2013.01); *G06F 16/438* (2019.01); *G06Q 10/06311* (2013.01); *G10L 25/48* (2013.01); *G16H 40/20* (2018.01)

(58) Field of Classification Search
CPC ......... G06Q 10/1093; G06Q 10/06311; G16H 40/20; G06F 16/438; G10L 25/48
See application file for complete search history.

(56) References Cited

U.S. PATENT DOCUMENTS

| 9,468,401 | B2* | 10/2016 | Van Hasselt | A61B 5/121 |
|---|---|---|---|---|
| 2010/0174699 | A1* | 7/2010 | DeRoche | G06Q 10/109 |
| | | | | 707/707 |
| 2014/0013271 | A1* | 1/2014 | Moore | G06F 3/04883 |
| | | | | 715/792 |
| 2015/0106349 | A1* | 4/2015 | Kitamorn | G06F 3/04817 |
| | | | | 707/706 |
| 2016/0275457 | A1* | 9/2016 | Dhillon | G06Q 10/1095 |
| 2016/0350722 | A1* | 12/2016 | Walker | G06Q 10/1093 |
| 2016/0361030 | A1* | 12/2016 | Buresh, II | G16H 20/40 |
| 2020/0286603 | A1* | 9/2020 | Ajilore | G16H 20/70 |

* cited by examiner

*Primary Examiner* — William L Bashore
*Assistant Examiner* — Gregory A Distefano
(74) *Attorney, Agent, or Firm* — Walter Haverfield LLP; Sean Mellino; James Pingor

(57) ABSTRACT

The innovation disclosed and claimed herein, in one aspect thereof, comprises systems and methods of remote scheduling of calendar and other means based queues and reminders to a user of a presentation device. The user of the presentation device may be suffering from a progressive cognitive disorder, and the queues and other care provided may be provided remotely by a loved one or other administrator.

15 Claims, 7 Drawing Sheets

REMOTE CARE SYSTEM

CROSS-REFERENCE TO RELATED APPLICATIONS

This application claims the benefit of U.S. Provisional Application Ser. No. 62/724,845, filed Aug. 30, 2018, and entitled "REMOTE CARE SYSTEM," the entirety of which is expressly incorporated herein by reference.

SUMMARY

The following presents a simplified summary of the innovation in order to provide a basic understanding of some aspects of the innovation. This summary is not an extensive overview of the innovation. It is not intended to identify key and/or critical elements of the innovation or to delineate the scope of the innovation. Its sole purpose is to present some concepts of the innovation in a simplified form as a prelude to the more detailed description that is presented later.

The disclosed innovation relates generally to providing remote personal non-medically licensed care through monitoring and task assistance. More particularly, the disclosed innovation relates to a system and method of remotely assisting end users with task queues associated with cognitive functioning.

The innovation provides an integrated advance in monitoring and assisting selected individuals that may be cognitively impaired or that may be benefited with aspects of the innovation. An example of the innovation may be an enhanced device or system making use of electronic calendaring (either third party calendaring or otherwise) by augmenting with integrated notes capability as well as integrated specific direct records concerning users for both scheduling and notification capabilities. Provisions through a notification component may be—through reference to a records module—may provide in several embodiments, the provision of notifications may be provided by one or more of static text, scrolling text, flashing text, and/or audio (including examples of standard voice selections or recorded or rendered personal voice selections, and/or chimes, musical notes and the like). Thus, accommodations may be made for various impairments, such as for example, hearing impairments, visual impairments and the like. It is to be appreciated that while many examples are provided in regards to interactions with users suffering from impaired and deteriorating mental cognition conditions such as Alzheimer's and dementia patients, many other uses are contemplated. The innovation is thus valuable to most any user that may benefit from assistance with daily orientation using visible and audible notes keyed by a records module in an ordered combination with a scheduling component and a notification component.

The innovation is configured to use electronic calendars (either third party calendars, for example, Google calendars, or otherwise), and configures a display on a presentation device to present at least a current day, date and time. In some embodiments, a general time of day, such as for example, "Morning," Afternoon," "Night" and the like may be displayed. In some embodiments, capabilities may include display of daily event schedules and/or a monthly calendar or pictures or video. Both standard and customizable voice notes may be used. It is to be appreciated that user conditions may be tracked and tonal conditions may be aligned with certain conditions. For example, voice tones of a supporting and patient nature may be used in certain conditions, while in other conditions in which an imperative action on the part of the user is desired, a more strident or stern tone may be provided. In some embodiments, the innovation may be controlled by an administrator using mobile technology via a smartphone, tablet, personal computer, Internet of Things (IoT) devices, and the like. Data (such as schedules, messages, pictures, videos and the like) may be entered by an administrator remotely, coordinated in a records module and a scheduling component, and through a notification component transferred to a presentation device via most any network or cloud technology. An administrator may be one or more caregivers or other person or persons. An administrator may be a super-user, a paying client, a care-giver, an onsite medical supervisor, a facility manager or the like. It is to be appreciated that transferring may be by downloading, streaming, or other mechanisms. Embodiments may include presentations provided in a "read only/display only" format to a user's living quarters. In some embodiments, a display device may be a television screen using an Android or Apple device or a stand-alone smart television. Similar to data transfer, an administrator may transfer application software to a local device, and the system may interact via the transferred software through telecommunication channels either to a processor or directly to a display of an Android or Apple box, smart television, tablet, IoT device, or the like. In an embodiment, controlling device may be preloaded with application software and need not require an administrator to have the application transferred. It is to be appreciated that a local device may be controller device, as disclosed above with an administrator using mobile technology. In this manner, a local device may be a mobile device and need not be located near a user, and control may be remote from a user. In some embodiments, data management by an administrator may be enabled on the administrator's device. Communicative connection may be provided over, but not limited to, the internet, intranet, the air waves, Wi-Fi, Bluetooth, Mobile Data and the like, and by smartphone, PDA, tablet, computing device, IoT device, or the like to another smartphone, PDA, tablet, computing device, IoT device, or other configured viewing apparatus, and the like. It is to be appreciated that some embodiments may comprise a display device that may be configured to serve as an input device, capturing feedback that a notification component may obtain, for example, that queued task has been completed.

Input/output devices as described may be, but are not limited to, computers, smartphones, tablets, electronic pads, electronic watches, wearable electronic devices, enabled televisions, IoT devices and the like as understood in the art.

As set forth below, a system and method are described that will continuously or near continuously operate asynchronously over Internet, intranet, telephone and/or mobile phone, or via wireless connections using open standards, permitting access and distribution controls, antivirus protection, and encryption for privacy. In accordance with the disclosure, the present innovation will advantageously work across most all computer platforms and/or operating systems.

In aspects, the subject innovation provides substantial benefits in terms of automation and convenience by providing assistance in a number of forms including cognitive, calming care, and humane treatment that may be more accepting to the person receiving the assistance throughout a progression of that person's condition.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
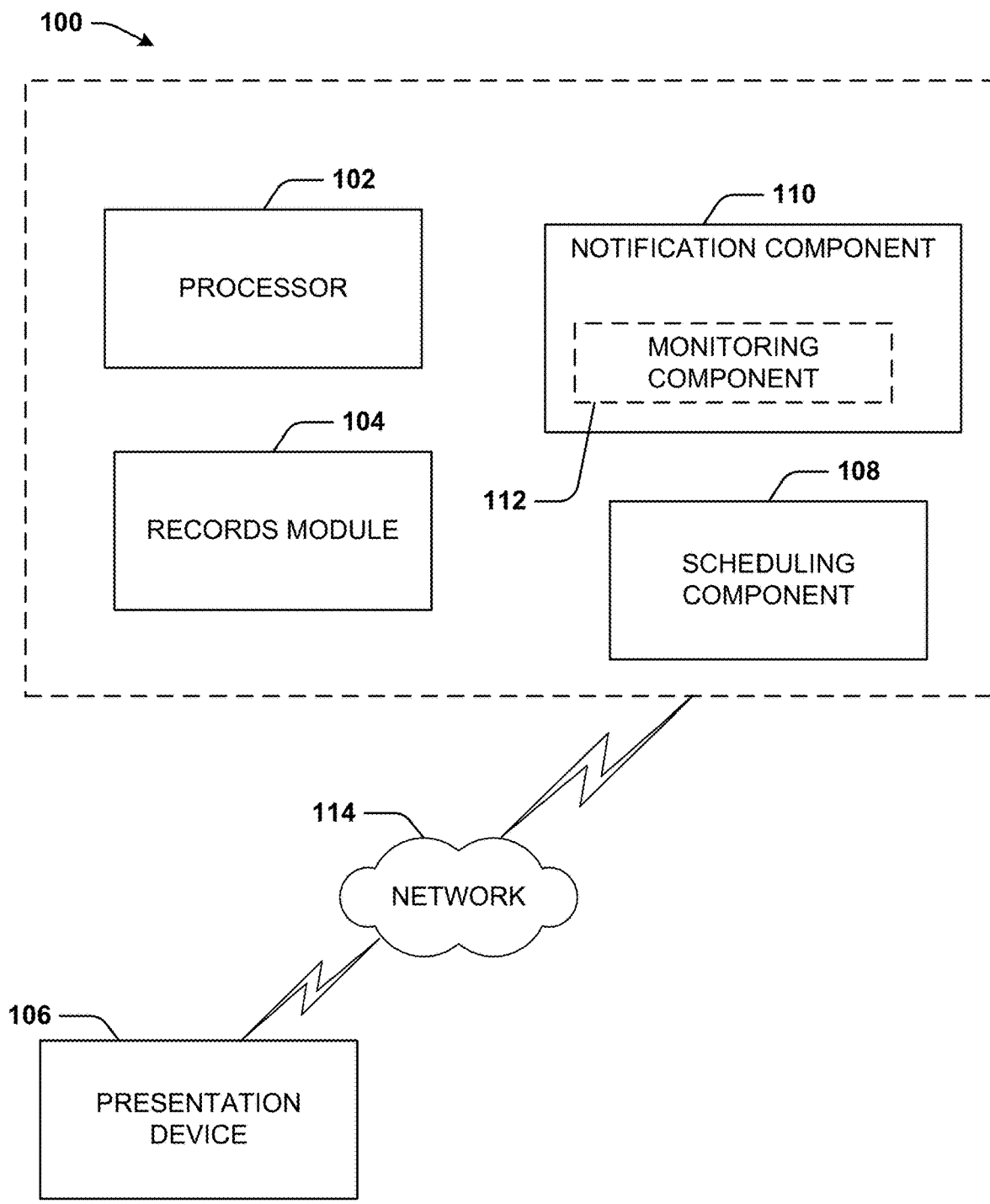
FIG. 1 illustrates an example component diagram of a system of the present innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, structures and devices may be shown in block diagram form in order to facilitate describing the innovation.

The innovation was spawned by noticing a lack of a meaningful ability of a non-medically trained family member to assist in the care of a loved one suffering from a worsening medical condition that affected the loved one's cognitive abilities, including the ability to remember to perform certain tasks. Often times, a caregiver may be precluded from having a personal and direct presence to monitor a person in need of care and may be unable to provide reminders in their physical absence. Complicating the situation is that the person in need of such care may be resistant to care and may not accept reminders from new people whom they cannot recognize due to memory impairment (of various types and degrees). Agitation that may result from unfamiliar care may only worsen the condition of the person already suffering from impairment, and such suffering is then magnified for the caregiver for whom, a conflict of time (and distance) may exist. The concerns to family members only grows worse, as a larger population shift is presenting an ever increasing burden on the ability of medically trained or skilled personnel to provide direct supervised care to an aging population, especially to a certain segment of the population that is experiencing growing need for assistance, particularly a need for mental reminders and caring interaction. User care for particular conditions may well be further impacted by a diminishing ability of the afflicted user to become familiar with a new caregiver due to particular degradations of cognitive abilities. Thus, inspiration was realized that a novel approach may be utilized with some innovation application of technology. Applying technology may provide real world improvements not only in how the technology is implemented, but in the direct methods for the provision of care that benefit both sides of those using the aforementioned technological innovations.

FIG. 1 illustrates a remote care system 100 in accordance with the present innovation. System 100 may comprise a processor 102. In some embodiments, system 100 may comprise a number of components and that processor 102 may provide the control of the system, including control of content, options, and configurations. It is to be appreciated that configurations may be modified or changed, and control of such modifications or changes may rest with processor 102. System 100 may be comprised of a records module 104. Records module 104 may be a database structure. Alternatively, a remote database structure (not shown) may be accessible by records module 104. Records module 104 will thus have access to (and control) records related to the system and its operation. These records may include administrator data and settings, user data and settings, and other data and settings, including, for example, medical device (not shown) data and settings, and presentation device 106 data and settings. It is to be appreciated that a records module 104 may contain or access a database that contains pertinent records, in that pertinent records may relate to administrative data and settings, user data and settings, and a presentation device data and settings. It is to be appreciated that presentation device 106 may be associated with one or more end users. In an embodiment, each end user may be associated with their own presentation device. In other embodiments, an end user may be associated with a plurality of presentation devices. It is to be appreciated that an end user may have a plurality of presentation devices considered as their own. In other words, it is contemplated that users, presentation devices and controls may be provide in one to one, one to many, many to one and many to many configurations. It is to be appreciated that one or more administrators may be nested within the one or more controls aspect.

System 100 may also comprise scheduling component 108. Scheduling component 108 is capable of interfacing with records module 104 and calendaring software (such as third party calendaring, for example, Google Calendar, or otherwise), in order to provide information to create a schedule according to various inputs which may be from at least records module 104.

System 100 may comprise notification component 110. In some embodiments, notification component 110 may comprise a monitoring component 112. It is to be appreciated that in some embodiments, monitoring component 112 may be a separate component in system 100. Monitoring component 112 may be configured so as to be able to monitor and receive inputs from presentation device 106. Notification component 110 is configured to be able to employ schedule and other information as set by scheduling component 108 in relation to records module 104. It is to be appreciated that notification component 110 operates in real time or near real time through scheduling component 108 in order to provide a presentation at presentation device 106 of selected items, and that the presentation of selected items may be per selected conditions as contained in records module 104.

In some embodiments, presentation device 106 may be located remotely from processor 102. For such embodiments, it is to be appreciated that notification component 110, monitoring component 112 and presentation device 106 would be capable of being in communicative contact. Communicative contact may be through a network 114, such as the Internet, or local network or wide area network, or the like.

Figure 2:
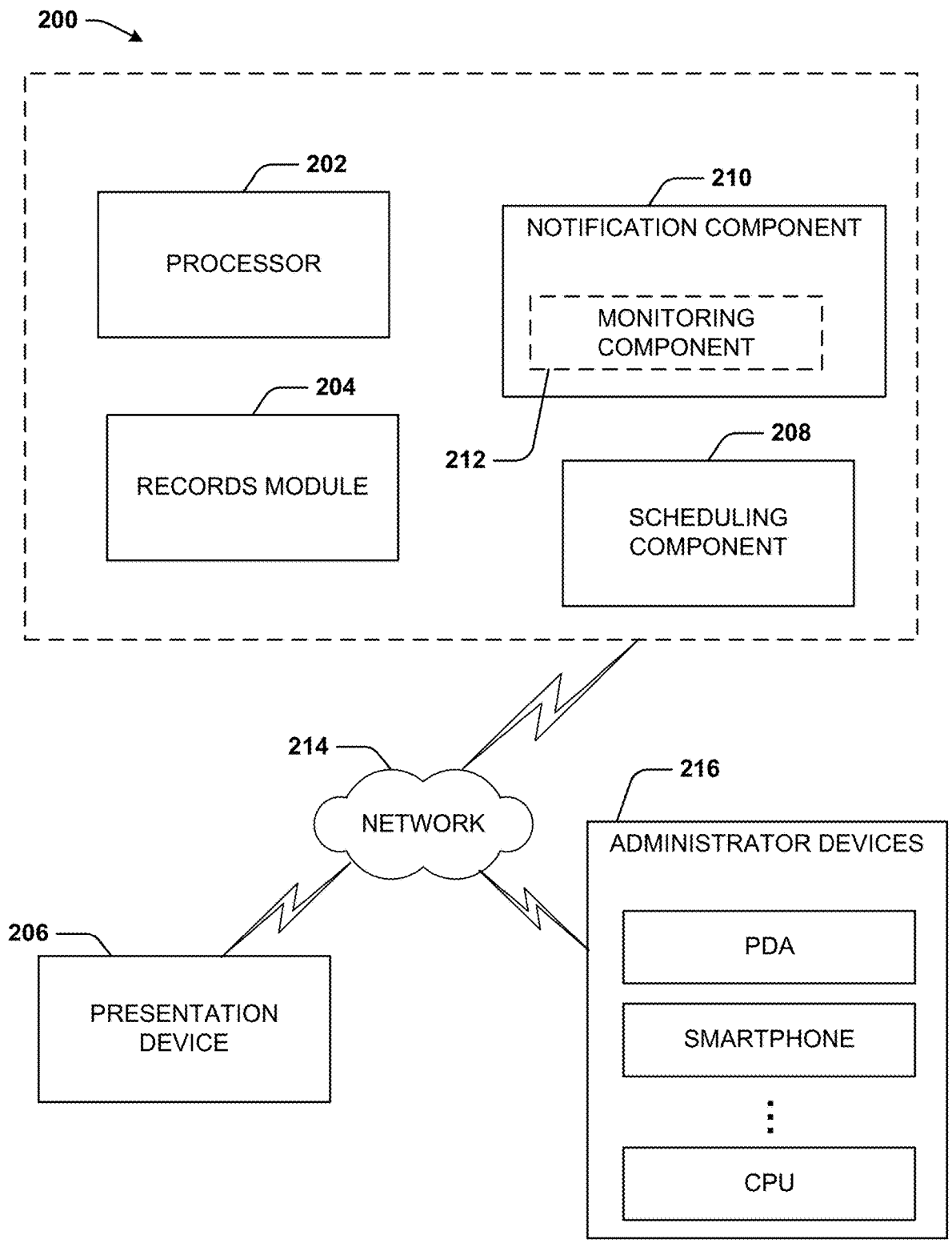
FIG. 2 illustrates an example component diagram of a system of the present innovation.

Turning to FIG. 2, an embodiment of remote care system 200 in accordance with the present innovation is illustrated. System 200 may comprise a processor 202. In some embodiments, system 200 may comprise a number of components and that processor 202 may provide the control of the system, including control of content, options, and configurations. It is to be appreciated that configurations may be modified or changed, and control of such modifications or changes may rest with processor 202. System 200 may be comprised of a records module 204. Records module 204 may be a database structure. Alternatively, a remote database structure (not shown) may be accessible by records module 204. Records module 204 will thus have access to (and control) records related to the system and its operation. These records may include administrator data and settings, user data and settings, and other data and settings, including, for example, medical device (not shown) data and settings, and presentation device 206 data and settings. It is to be appreciated that presentation device 206 may be associated with one or more end users. In an embodiment, each end user will be associated with their own presentation device. In other embodiments, an end user may have more than one presentation device, and associations may be made across the plurality of end user devices.

System 200 may also comprise scheduling component 208. Scheduling component 208 is capable of interfacing with records module 204 and calendaring software (such as, for example, Google Calendar, Apple iCal, or the like—third party or otherwise), in order to provide information to create a schedule according to various inputs which may be from at least records module 204.

System 200 may comprise notification component 210. In some embodiments, notification component 210 may comprise a monitoring component 212. It is to be appreciated that in some embodiments, monitoring component 212 may be a separate component in system 200. Monitoring component 212 would be configured so as to be able to monitor and receive inputs from presentation device 206, for example, monitoring component 212 may be configured to receive touch screen input from presentation device 206. Additionally or alternatively, presentation device 206 may be configured with input means, such as audio input means, data entry means such as a keyboard or virtual keyboard, and the like. An embodiment may use this capability to be able to receive input when queued events and tasks are completed by a user. Notification component 210 is configured to employ schedule and other information as set by scheduling component 208 in relation to records module 204. It is to be appreciated that notification component 210 operates in real time or near real time through scheduling component 208 in order to provide a presentation at presentation device 206 of selected items, and that the presentation of selected items may be per selected conditions as contained in records module 204. In an embodiment, monitoring component 212 receives input through presentation device 206, devices associated with presentation device 206 (not shown), or a combination of each. Input received may include task completion or event status information as queued events transpire and tasks are completed by a user.

In some embodiments, presentation device 206 may be located remotely from processor 202. For such embodiments, it is to be appreciated that notification component 210, monitoring component 212, and presentation device 206 would be capable of being in communicative contact. Communicative contact may be through a network 214, such as the Internet, or local network or wide area network, or the like.

System 200 may comprise administrator device 216 that may be communicatively connected, for example through network 214, with processor 202. It is to be appreciated that administrator device 216 may be a PDA, a smartphone a tablet, a computer, an IoT device, or the like. Administrator device 216 may provide inputs as to selected messages and events that are to be used for one or more users at a presentation device(s) 206. Administrator device 216 may also be provided outputs such as notifications from notification component 210. For example, predetermined or amended rules in records module 204 may include a disruption notification rule set. Upon determination that a presentation device or other element in remote care system 200 has lost power, become inoperable, or network service has been disrupted, a notification from notification component 210 may be supplied to administrator device 216 in the form of an alert. In an embodiment, an alert may indicate a type of disruption, a level of duration of the disruption, an indicator of a severity of the disruption, a recommendation related to the disruption or a combination of these notifications. It is to be appreciated that in an embodiment, a disruption of network service may involve an alternative path of notification from notification component 210 to administrator device 216 (not shown). Disruption notification rule set may be configurable at various levels including one or more individual users, presentation devices, and one or more administrators.

In regards to a provision of inputs, administrator device 216 may, in conjunction with rules and or settings contained in records module 204, be able to input and or amend records in records module 204. It is to be appreciated that embodiments for multiple users may be provided, with records module 204, scheduling component 208, notification component 210, and monitoring component 212 selectively aligned with a particular user. For example, multiple user settings may include family integrated calendaring, diagnosis grouping, grade level grouping, and/or employee position groupings. It is also to be appreciated that embodiments for multiple administrators may be provided, with records module 204 reflecting a plurality of administrators and rule sets configurable to provide universal or varied administration capabilities to the one or more administrators. It is to be appreciated that records may include items that affect schedules through scheduling component 208. Records may also include new or amended events associated with calendaring software, or most any electronic media that may be associated with other devices and third party services (for example, and without limitation, items captured from such as Facebook posting, twitter feed, personal photograph and video clip. Capture may occur—for example, through a smartphone. Administrator device 216, per rules and permissions captured in records module 204, may amend the content and presentation details that notification component 210 may supply to one or more presentation device 206.

It is to be appreciated that events or tasks can be scheduled for a designated time or without a designated time and instead, for example, be driven by a particular day or portion of day, such as "morning" being associated with a certain task. Scheduling component 208 may predetermine timing for activation of messages and the like on the presentation device 206. Message activation may be visual or aural or a combination of visual and aural. Aural messaging may be provided in a choice of standard voices or may be captured (or rendered) in voices that may be familiar to an end user.

It is to be appreciated that different familiar voices to the end user, including without limitation the voice of the end user himself, may be used based on at least administrator choice. In some embodiments this choice may be presented on the fly and in some embodiments, this choice may be reflected in records module 204. It is also to be appreciated that choices may change based on user condition, such as, for example, disease progression and loss of recognition of voices by a user throughout a progression. In some embodiments, choices may change based on feedback received through monitoring component 212.

Management may be undertaken via a smartphone, tablet, personal computer, IoT device, or the like. Accessibility may be shared among selected groups, including, for example, trusted family members, designated or authorized workers, or the like. Schedule, repeat, and customize audible voice notes and queues may be managed. The ability to record and customize personal voice notes and queues in a loved one's own voice may be provided. In other embodiments, standardized, pre-recorded audible notes and queues may be included. In other embodiments, notes may be rendered in a chosen voice, including the voice of a caregiver, loved one or the like. Managed conditions in relation to impairments, such as for example, hearing or visual impairment may be provided in embodiments.

Daily day and date announcements may be provided on simple, easy-view date and time display panels. In some embodiments, daily events may display in large, easy-to-read text. Some embodiments may feature auditory and/or picture/video accompaniment to an event display.

As discussed, an embodiment may include the ability to manage event notifications and other task queuing via a suitably configured smartphone, tablet, personal computer, IoT device or the like. It is to be appreciated that in such an embodiment, the ability to update notes and queuing from a distance from a user is afforded, even from the convenience of a caregiver's home, office, or even while a caregiver may be traveling. Updates may include adding new queues, editing existing ones, or deleting obsolete notes. As discussed, abilities include scheduling repeat or non-repeating events, and the ability to customize audible voice notes and queues. With the system, it is to be appreciated that one may create a daily voice queue. One may schedule queues to announce each day, each weekday, weekends only, or a combination as may be desired. One may schedule repeats for example, only on Wednesdays. One may repeat an audible queue each day, week, month, or year. Records module, such as records module 104 or 204 may capture choices of a beginning date and ending date for voice or text queues, as well as other control conditions. Voice queues may be provided in choices of standardized, pre-recorded voice queues for common reminders, as well as the ability to provide comfort and reassurance for a user from a caregiver through customizing, recording and/or rendering voice queues in a selected personal voice, even of the voice of the user.

Figure 3A:
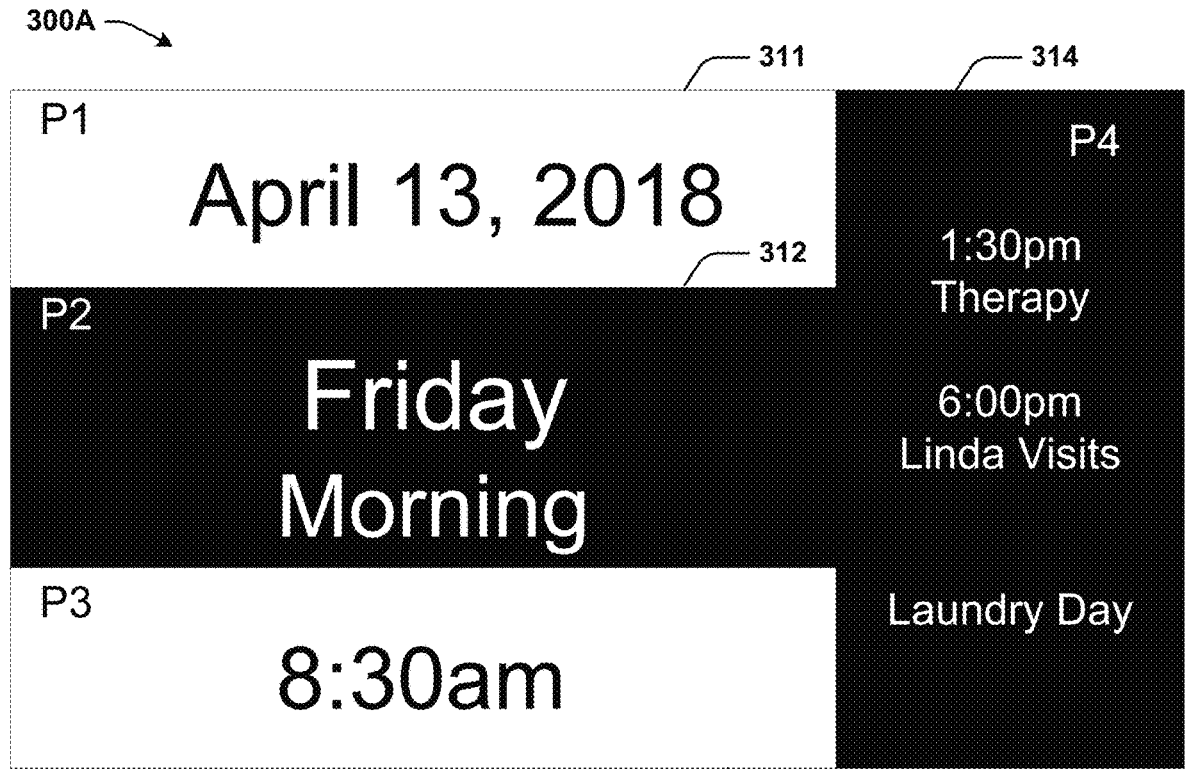
FIGS. 3A-3C illustrate example embodiments of a display in accordance with the present innovation.
Figure 3B:
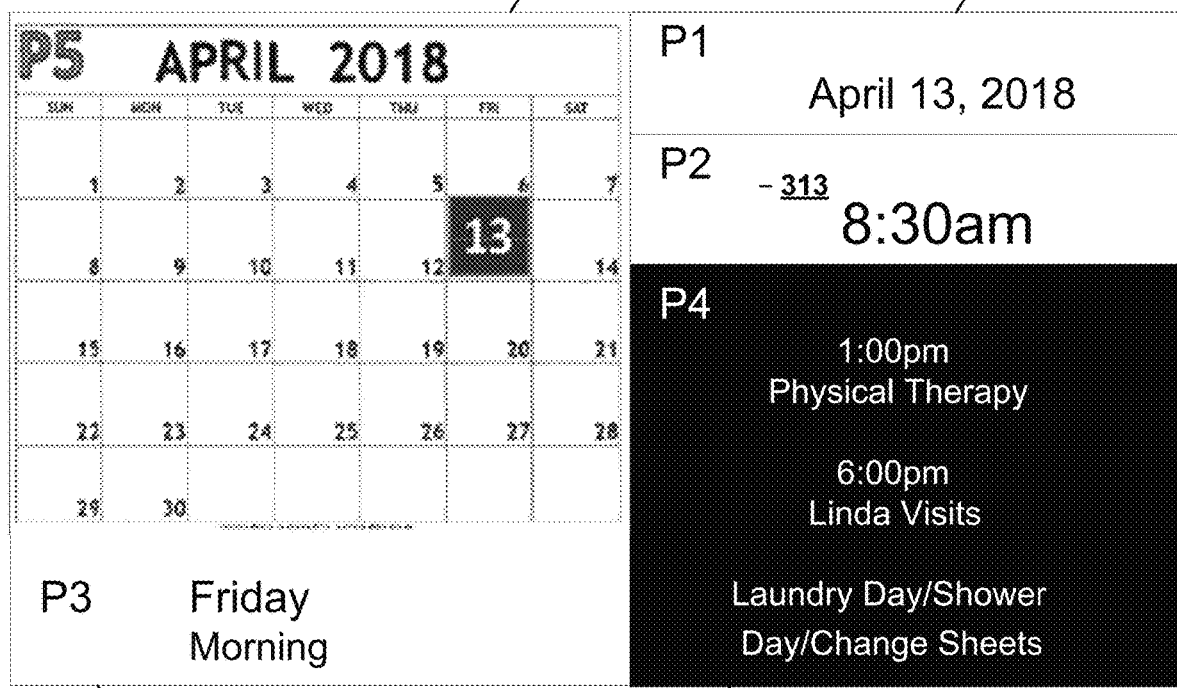
Figure 3C:

Turning now to FIGS. 3A through 3C, various example presentation screens are disclosed. It is to be appreciated that presentation screens are examples of the capabilities that notification component, for example notification component 210 of system 200 or notification component 110 of system 100 may be configured to cause to be displayed on presentation device 206 or presentation device 106 respectively. It is also to be appreciated that the number of panels as well as the content and display options provided may be controlled by processor 102 or 202 or by administrator through administrator device 216 as the case may be. These presentation capabilities are determined at least in part by the records module 104 of system 100 or records module 204 of system 200, for example. It is also to be appreciated that selections of presentation options may vary from the following discussion, as some options from a particular figure may be interchanged with other options of another particular figure.

FIG. 3A may provide an additional panel 314. Panel 314 may provide visual and/or auditory reminders of scheduled events per the control of scheduling component 108 or 208. Panel 314 may provide for selective display of a predetermined number of tasks or events scheduled for the day. Tasks/events without a designated time may be displayed last or otherwise separated from tasks/events with designated times. Additionally or alternatively, a scrolling ticker may provide continual scrolling of customized notices, comments, or encouraging words. It is to be appreciated that panels may be configured to reflect inputs received, as discussed herein, and provide feedback as to confirmation of task status including for example, encouragement for completed tasks.

An embodiment may display events so as to list them in chronological order. As events are concluded or otherwise eliminated, event indicators may cease being displayed or prompted. For instance after 1:00 PM, a scheduled therapy session may be removed from the display, and a next event, for example, 6:15 PM event may be featured in a prominent location and an 8:00 PM event (for example, a John Wayne movie) would display in a less prominent location. Other events, such as an undesignated event, for example, Laundry Day/Shower Day/Change Sheets may remain in yet another less prominent location since such items do not have a specific time designation.

In some embodiments, audio announcements or event reminders may be preceded by an audible chime, or in some embodiments, a visual mechanism such as a flashing light or solid color indicator may be activated. In some embodiments, the system may play a standard or customizable voice note with each task or event. This chime may queue a user to listen for an upcoming voice note. The voice note audibly announces the associated calendar task or event. System options may provide the capability for an administrator to choose whether to announce the voice note, display the task/event, or both. Examples may include, but are not limited to the following:

| Time: | Scheduled: | Type | Audible Voice Note (Standard/Customizable): |
|---|---|---|---|
| 7:30 am | Mon-Fri | Audible | Good morning Dad, don't forget that breakfast is in 30 minutes. |
| 8:00 am | Mon-Fri | Audible and Text | Time to eat breakfast. |
| 8:30 am | Sat/Sun | Audible | Good morning Dad, don't forget that breakfast is in 30 minutes. |
| 9:00 am | Sat/Sun | Audible and Text | Time to eat breakfast. |
| 11:45 am | Sun-Sat | Audible | Lunch will be served in 15 minutes. |
| 12:00 pm | Sun-Sat | | Lunch Time |
| 1:00 pm | April 30 | Audible | Hi Dad, remember that you have a doctor's appointment at 3pm today. Linda will pick you up at 2:30pm. |
| 2:30 pm | April 30 | Text on Display | Time for Linda to pick you up for your doctor's appointment. |
| 3:00 pm | April 30 | Audible and | Doctor's Appointment at |

-continued

| Time: | Scheduled: | Type | Audible Voice Note (Standard/Customizable): |
|---|---|---|---|
|  |  | Text | the VA with Dr. Smilovich, primary care physician. |
| 4:45 pm | Sun-Sat | Audible | Dinner will be served in 15 minutes. |
| 5:00 pm | Sun-Sat | Audible | Time to eat dinner. |
| All Day | M/W/F | Text on Display | Take a walk down the hallways |

It is to be appreciated that embodiments may vary as to limit reminders based on at least Administrator choice, user cognitive state, or other considerations captured in Records Module. Additionally or alternatively, display panel 314 may be configured to display alternate day(s), or lists of events by swiping to the right or left (for example, a swipe left may provide past events, while a swipe right may provide future events. Rules within a records module, for example records module 104 or 204 may provide control of such a feature. It is to be appreciated that such rules may be modified, updated, or disabled with an administrator device, such as administrator device 216.

Turning to FIG. 3B, an example presentation panel configuration is shown that includes the types of information from panels included in FIG. 3A, as well as includes an additional panel 315. It is to be appreciated that specific panel location, prominence and size may be determined by rules set up in records module 104 or 204 or may be driven by scheduling component 108 or 208 or may be altered based on feedback received through monitoring component 112 or 212. Further, administrator device 216 may interact with various system components in order to amend or modify the location and/or prominence of the various panels. In FIG. 3B, panel 315 may provide an additional panel that may provide additional viewing material to one or more end users of presentation device 106 or 206. It is to be appreciated that the additional panel 315 may provide a fixed or static content, which may be amended or changed on a scheduled basis, for example as controlled by scheduling component 108 or 208, or may provide non-static content, for example, notification component 110 or 210 may be integrated with third party content providers and may stream content at panel 315. Alternatively, content of panel 315 may be provided as an internet web interface. Panel 315 may provide for capability of telehealth, or remote health care visits using a webcam system. Additionally, panel 315 may be configured to provide picture within a picture, with multiple feeds from a variety of sources, including but not limited to streaming television, internet, or other video feeds. It is to be appreciated that control of content on panel 315 may be controlled through records module 104 or 204 or may be locally influenced by inputs from configured presentation device 106 or 206.

Comparing FIG. 3B and FIG. 3C, panel 315 is shown as a static (updatable) monthly calendar page in FIG. 3B, and as a snapshot of an item (photo or video) in FIG. 3C. In FIG. 3C, 315 may be selected to show items that one or more users of presentation device 106 or 206 may find of emotional value and reassurance. It is to be appreciated that the particular image may be keyed to a user's condition, and that for those with cognitive disabilities, a familiar long-term memory visual may be provided. In some embodiments, the picture or video on panel 315 may be associated with the upcoming scheduled event. It is to be appreciated that combining a visual of person or item associated with long-term memory with the current scheduling reminder may provide a more beneficial queue to the user of presentation device 106 or 206. It is also to be appreciated that an administrator device 216 may provide real time or near real time queues or a caretaker may provide such queues to a records module 104 in a system that operates without administrator device 216. In such an embodiment, end user may be presented with pictures or video of family members, inspirational presentations, favorite scenes and the like that may provide comfort to the local user. It is to be appreciated that the innovation may provide comfort to a user by caregiver(s) by multiple modes: not only hearing a familiar voice, but also by visual association of familiar pictures related to the voice. In an embodiment, the system may provide the contents of the voice message in text form, which may aid cognition of a user.

In an embodiment, a viewable monitor may be provided to a user in his or her residence that displays a number of panels. As disclosed herein, panels may display the day of the week, general time of day (morning, afternoon, or night), exact time of day, and calendar date. Panels may also display events or tasks that may be scheduled for a designated time or as an all-day or undesignated time event. It is to be appreciated that notifications may occur throughout the day, or as predetermined. Notifications may be visual, as per the panels, as well as may be provided by auditory means, such as through speakers associated with a presentations device. Standardized or custom voice notes may be played at designated times based on the scheduled tasks or events and may be synced with a variety of the display panels. Display panels may be modified as is known in the art. It is to be appreciated that display panel configurations may be based on a user's limited cognitive abilities. Thus, the choice of displays, and prominence of the displays, as well as content of a display, may be keyed to a cognitive state of a user. For example, for an advanced state of cognitive impairment, a basic 3-panel display may be provided. The embodiment may comprise only basic day, date, and time functionality and includes basic standard or customized voice notes to announce current date and event queues. Such an option may provide voice notes recognizable by the user without overwhelming the user with too much information.

Figure 4:
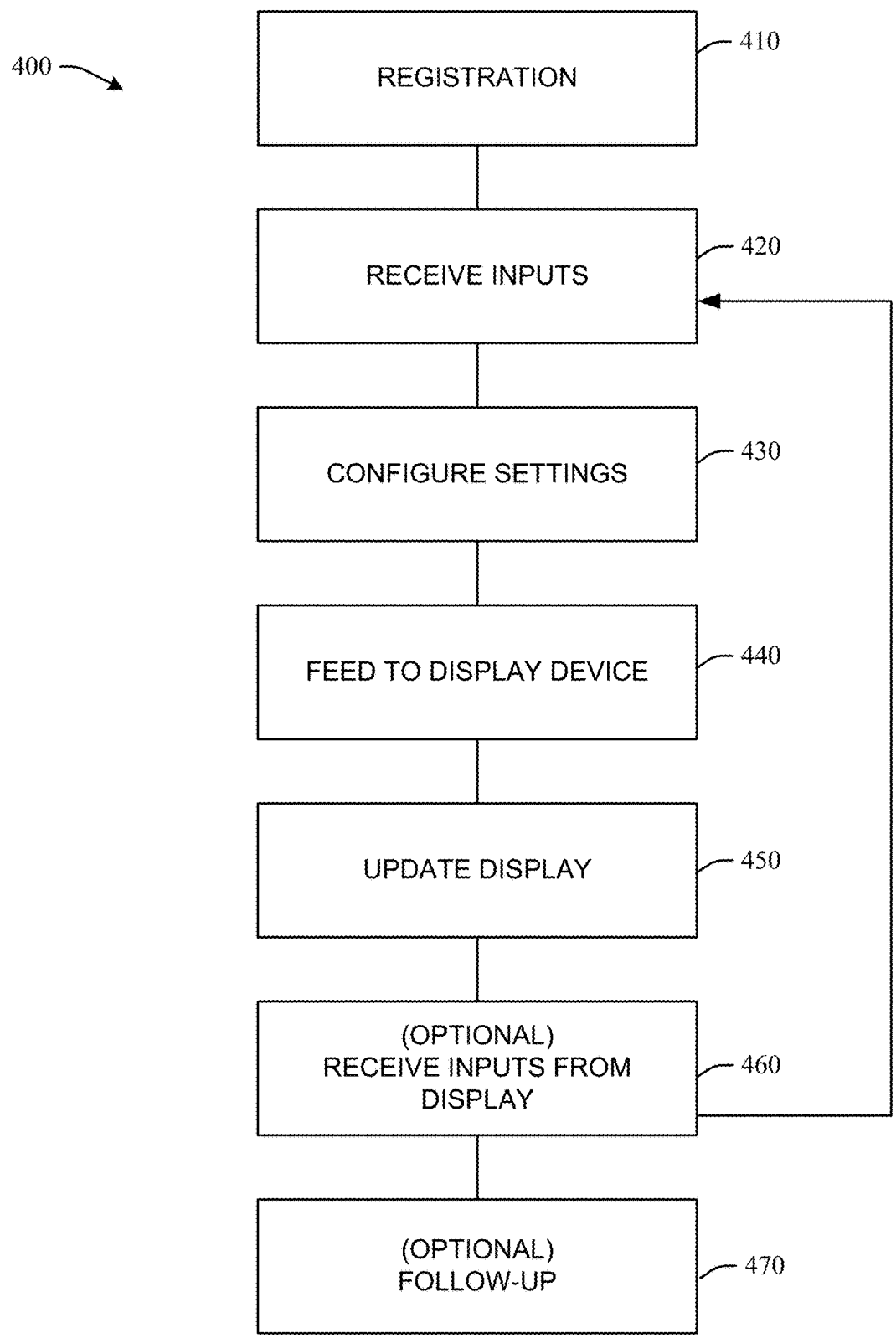
FIG. 4 illustrates a method in accordance with the present innovation.

Turning now to FIG. 4, an example method according to aspects of the innovation is presented. Method 400 may be initiated with registration step 410. Registration step 410 may include registration with a processor, for example processor 102 of system 100 or processor 202 of system 200. Registration step 410 comprises setting details into a records module, for example, records module 104 or 204. Records in records module 104 or 204 may comprise data and or settings related to one or more users of one or more presentation devices 106 or 206. Records may comprise rules and/or data that may assist a scheduling component such as scheduling component 108 or 208 and that may interact with calendaring functions as disclosed herein, or the like. These inputs to record module may comprise some or all of the receive inputs step 420. Additionally in some embodiments, receiving inputs step 420 may include the receiving of additional inputs, for example and without limitation, inputs from a pedometer, a wearable device and the like may be received. Receiving of additional inputs may be contemplated, for example with inputs received from monitoring component 112 or 212 or from amendments, modifications or additions per an administrator device (for example, administrator device 216 of system 200).

At step 430, the various inputs, including in some embodiments inputs from records module 104 or 204 inputs from monitoring component 112 or 212, inputs from administrator derive 216 and/or inputs from third party software or devices may be integrated and configured into a schedule controller, such as scheduling component 108 or 208. A schedule controller can then control timing, sequence, repetition, prominence settings and the like. Control commands may then be fed to a display device 440 through a notification component, for example, notification component 110 or 210, and then fed to a presentation device (such as for example one or more presentation devices 106 or 206 to one or more end users). Such notification may occur locally or non-locally as may be desired or set up through network 114 or 214, for example. At step 450, a display is updated. For example, in FIG. 3A through 3C displays on one or more panels may be updated. It is to be appreciated that the panels may update in association with each other or otherwise. It is also to be appreciated that updates to the display may occur in either visual or aural modes or both. At step 460, an embodiment may include an optional ability to receive inputs through a display (or other monitoring component), for example, presentation device 106 or 206 may be configured to receive user input and through monitoring component 112 or 212 receive inputs process inputs into a processor 102 or 202 or provide feedback to a an administrator device 216. It is to be appreciated that inputs may be received through devices other than a display. For example and without limitation, inputs may be received from a pedometer, a wearable device and the like. Such feedback may be in real time or near real time. Alternatively, feedback may be captured in records module (for example records module 104 or 204) and may be accessed or played back at a later time. At step 470, in some embodiments, follow-up to the user may be provided and may be based on various interactions and captured through monitoring component 112 or 212. It is to be appreciated that such follow-up may be provided in preselected modes including, but not limited to, pre-recorded (or live) voice sections that would be familiar to the user (for example, a recognizable voice during a disease progression such as Alzheimer's disease). Such modes may include ether user's own voice, or a familiar voice of a loved one.

Figure 5:
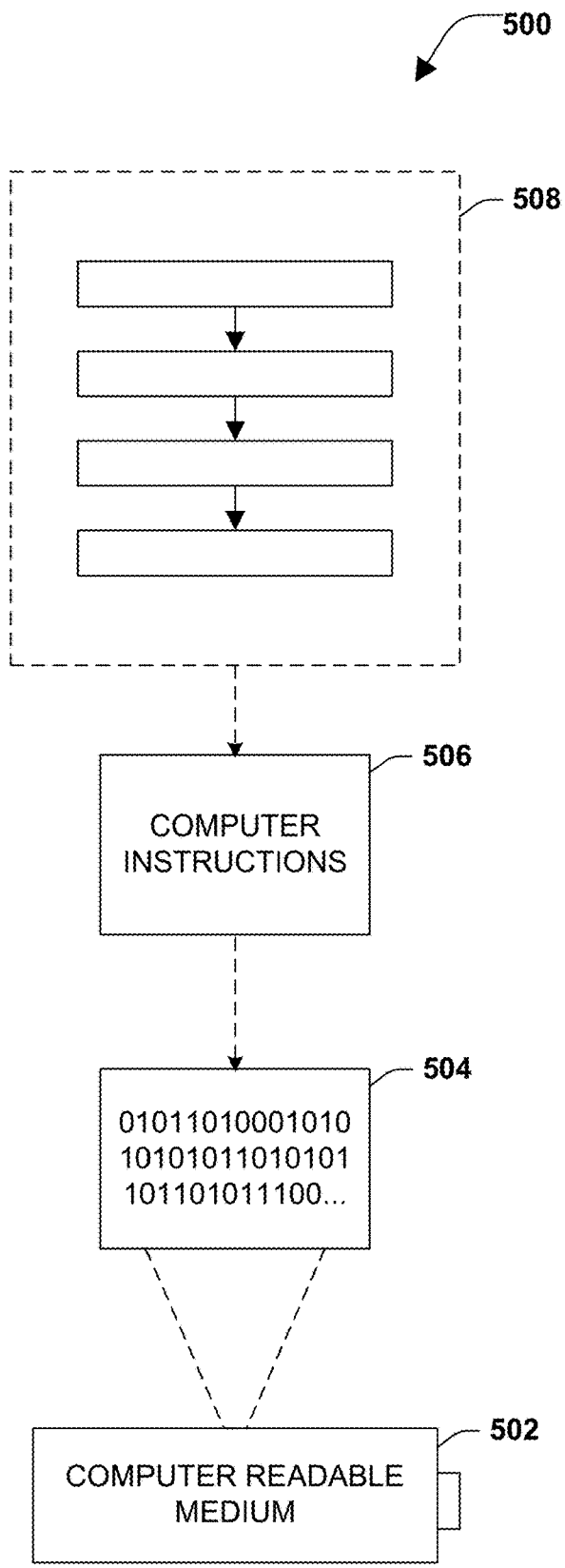
FIG. 5 illustrates a computer-readable medium or computer-readable device comprising processor-executable instructions configured to embody one or more of the provisions set forth herein, according to some embodiments.

Still another embodiment in accordance with the present innovation can involve a computer-readable medium comprising processor-executable instructions configured to implement one or more embodiments of the techniques presented herein. An embodiment of a computer-readable medium or a computer-readable device that is devised in these ways is illustrated in FIG. 5, wherein an implementation 500 comprises a computer-readable medium 502, such as a CD-R, DVD-R, flash drive, a platter of a hard disk drive, etc., on which is encoded computer-readable data 504. This computer-readable data 504, such as binary data comprising a plurality of zero's and one's as shown in 504, in turn comprises a set of computer instructions 506 configured to operate according to one or more of the principles set forth herein. In one such embodiment 500, the processor-executable computer instructions 506 is configured to perform a method 508, such as at least a portion of one or more of the methods described in connection with embodiments disclosed herein. In another embodiment, the processor-executable instructions 506 are configured to implement a system, such as at least a portion of one or more of the systems described in connection with embodiments disclosed herein. Many such computer-readable media can be devised by those of ordinary skill in the art that are configured to operate in accordance with the techniques presented herein.

Figure 6:
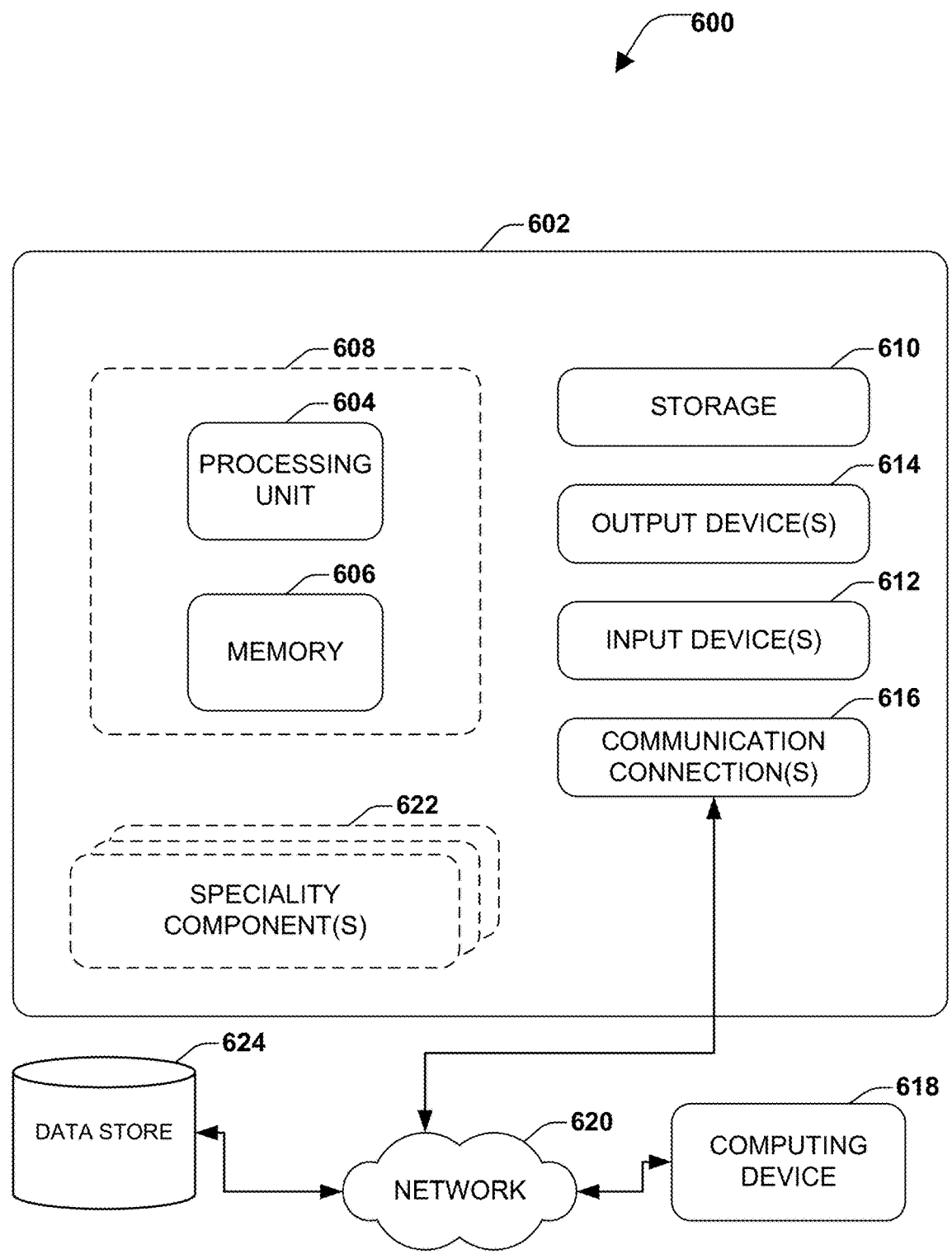
FIG. 6 illustrates a computing environment where one or more of the provisions set forth herein can be implemented, according to some embodiments.

With reference to FIG. 6, and the following discussion, a description of a suitable computing environment in which embodiments of one or more of the provisions set forth herein can be implemented is provided in accordance with the present innovation. The operating environment of FIG. 6 is only one example of a suitable operating environment and is not intended to suggest any limitation as to the scope of use or functionality of the operating environment. For example, suitable computing devices include, but are not limited to, personal computers, server computers, hand-held or laptop devices, mobile devices, such as mobile phones, Personal Digital Assistants (PDAs), media players, tablets, IoT devices and the like, multiprocessor systems, consumer electronics, mini computers, mainframe computers, distributed computing environments that include any of the above systems or devices, and the like.

Generally, embodiments are described in the general context of "computer readable instructions" being executed by one or more computing devices. Computer readable instructions are distributed via computer readable media as will be discussed below. Computer readable instructions can be implemented as program modules, such as functions, objects, Application Programming Interfaces (APIs), data structures, and the like, that perform particular tasks or implement particular abstract data types. Typically, the functionality of the computer readable instructions can be combined or distributed as desired in various environments.

FIG. 6 illustrates a system 600 comprising a computing device 602 configured to implement one or more embodiments provided herein. For example, system 600 may implement system 100 or system 200. In one configuration, computing device 602 can include at least one processing unit 604 and memory 606. For example, in implementing system 100, processing unit 604 may be implemented as processor 102. For another example, in implementing system 200, processing unit may be implemented as processor 202. Depending on the exact configuration and type of computing device, memory 606 may be volatile, such as RAM, non-volatile, such as ROM, flash memory, etc., or some combination of the two. This configuration is illustrated in FIG. 6 by dashed line 608.

In these or other embodiments, device 602 can include additional features or functionality. For example, device 602 can also include additional storage such as removable storage or non-removable storage, including, but not limited to, magnetic storage, optical storage, and the like. Such additional storage is illustrated in FIG. 6 by storage 610. In some embodiments, computer readable instructions to implement one or more embodiments provided herein are in storage 610. Storage 610 can also store other computer readable instructions to implement an operating system, an application program, and the like. Computer readable instructions can be accessed in memory 606 for execution by processing unit 604, for example.

The term "computer readable media" as used herein includes computer storage media. Computer storage media includes volatile and nonvolatile, non-transitory, removable and non-removable media implemented in any method or technology for storage of information such as computer readable instructions or other data. Memory 606 and storage 610 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 602. Any such computer storage media can be part of device 602.

The term "computer readable media" includes communication media. Communication media typically embodies computer readable instructions or other data in a "modulated data signal" such as a carrier wave or other transport mechanism and includes any information delivery media. The term "modulated data signal" includes a signal that has one or more of its characteristics set or changed in such a manner as to encode information in the signal.

Device 602 can include one or more input devices 612 such as a keyboard, a mouse, a pen, a voice input device, a touch input device, infrared cameras, video input devices, or any other input device known in the art. One or more output devices 614 such as one or more displays, speakers, printers, or any other output device can also be included in device 602. The one or more input devices 612 and/or one or more output devices 614 can be connected to device 602 via a wired connection, wireless connection, or any combination thereof. In some embodiments, one or more input devices or output devices from another computing device can be used as input device(s) 612 or output device(s) 614 for computing device 602. Device 602 can also include one or more communication connections 616 that can facilitate communications with one or more other devices 618 by a communications network 620, which can be wired, wireless, or any combination thereof, and can include ad hoc networks, intranets, the Internet, or substantially any other communications network that can allow device 602 to communicate with at least one other computing device 618.

Specialty components 622 may include a number of components to the system that may add integration of features, either as modules or as integrations to third party modules. For example, specialty components may include positive reinforcement module. Positive reinforcement modules may provide cognitive charting and progress, and provide feedback to display on a presentation device, for example, an auto acknowledgment capability may be provided that provides positive reinforcement for when a user stands up, performs a specified task, such as walking. Such items may be captured by a monitoring component such as monitoring component 112 or 212 and logged in a records module such as records module 104 or 204, wherein rules may be set to provide the positive feedback to the user.

Specialty components may also include presentation device add-ons, such as auto-record functionality, streaming or projecting of streaming content. Specialty components may include a pro-active or interactive maintenance feature that may provide for condition based maintenance event creation. Such capability may include predictive failure capability. Specialty components 622 may also include interactive assistance to coordinate interaction with third party verbal request platforms for example, third party verbal request platforms marketed under trade names such as "Hey Google," "Alexa," and "Siri."

Additionally or alternatively, specialty components 622 may include or be configured to interface with medical equipment monitoring devices and capabilities, for example, Bluetooth Sync with Medical Monitoring Devices (BM)—Blood Sugar Level Monitoring, HR, Activity, Steps, Pacemaker, and the like. It is to be appreciated that in some embodiments, medical information obtained through a configured interface may be anonymized to limit, alleviate, or remove governmental regulations, while serving to amend established rules and other controls in a Records Module.

Specialty components 622 may in some embodiments be adapted to include motion detection and programming for motion detection coupled with alarm rules. For example, motion detection for living quarters may prompt an alarm if no motion is detected during designated hours for which motion would be expected. Conversely, other rules may provide for an alarm to be prompted if motion is detected during designated hours for which motion would not be expected. For example, upon an initial motion detection for a new day, as noted by a monitoring component such as monitoring component 112 or 212, the system may provide through a notification component, such as notification component 110 or 210, a "My Day Announcement" for example: "Good Morning Ed, Today is Thursday, Apr. 26, 2018. You are in Chagrin Falls, Ohio. The weather is sunny with no rain and a high of 56 degrees." It is to be appreciated that other daily activities, events and queues, as may be provided by a scheduling component such as scheduling component 108 or 208, could also be announced. It is to be appreciated that motion detection may comprise various types or modes, including without limitation passive infrared, microwave, dual technology motion sensors, area reflective type, ultrasonic, vibration, and the like.

Specialty components 622 may also be especially adapted input device elements. For example, specialty components 622 may comprise RFID functionality, allowing a scan of a watch, wristband or other item to check-in or check-out, or to signify input that a task has been completed. Additionally or alternatively, such devices may be configured to receive notifications from a notification component, for example, notification component 110 or 210 and such notifications may provide haptic functionality. That is, the receiving device may shake or vibrate as part of the provided notification. Such specialty component 622 may be a part of monitoring component, such as monitoring component 112 or 212, as disclosed herein.

It is to be appreciated that the system may include hardware such as Android/iOS television box or Android/iOS compatible smart television, smartphone, tablet, personal computer, IoT device or the like, and an Internet connection. Most any computing operating systems are compatible, for example compatibility may include operating systems marketed under trade names such as Android, iOS, Amazon Fire OS, FireTV, Firesticks and the like.

Software components of the system may include software configured to be run on a processor that provides the functionality of the records module, the scheduling component and the notification and monitoring components. Additionally, software components may include modules that may be loaded on a computing device, such as a PDA, smartphone, tablet, standalone computer, IoT device or the like and that provide functionality described herein related to administrative functions. That is, a computing device may be configured to be an administrator device, such as administrator device 216 of system 200. It is to be appreciated that software components may also include third party software such as to enable interaction with third party applications (for example, a Google account that may provide interaction with a Google calendar).

As used in this application, the terms "component", "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, or a computer. By way of illustration, both an application running on a controller and the controller can be a component. One or more components residing within a process or thread of execution and a component may be localized on one computer or distributed between two or more computers. As noted herein, an administrator may be one or more caregivers or other person or persons. An administrator may be a super-user, a paying client, a caregiver, an onsite medical supervisor, a facility manager or the like.

Furthermore, the claimed subject matter can be implemented as a method, apparatus, or article of manufacture using standard programming or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

While certain ways of displaying information to users are shown and described with respect to certain figures as screenshots, those skilled in the relevant art will recognize that various other alternatives can be employed. The terms "screen," "web page," "screenshot," "view," and "page" are generally used interchangeably herein. The pages or screens are stored and/or transmitted as display descriptions, as graphical user interfaces, or by other methods of depicting information on a screen (whether personal computer, PDA, mobile telephone, or other suitable device, for example) where the layout and information or content to be displayed on the page is stored in memory, database, or another storage facility.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computerized system for improving electronic processing related to remote queuing and provisioning of tasks for a care-related remote situation, the system comprising:
    a records module that contains or accesses a database of pertinent records,
    wherein pertinent records relate to administrative data and settings, user data and settings, and a presentation device data and settings;
        a processor that executes instructions, wherein the execution implements action for a scheduling component and a notification component,
            wherein the scheduling component in conjunction with a calendaring application, integrates the data and settings of administrative, user and presentation device from the records module into a controlled schedule,
                wherein the controlled schedule comprises presentation aspects of at least timing, duration, and actions taken when time passes and actions are completed; and
            wherein the notification component is driven by the scheduling component and provides to a presentation device a set of queues and notifications, and wherein the notification component is configured to provide at least one of read only/display only notifications, static notifications, dynamic notifications, notifications rendered in text, visual, aural or combinations of text, visual and aural renderings, and wherein the notifications are associated with a condition of the user, and
            wherein the aural renderings are provided in at least one of a standard voice and a user-familiar voice, wherein the user-familiar voice comprises pre-recorded notifications or notifications rendered in the user-familiar voice without being pre-recorded, and wherein the aural renderings comprise tonal qualities based at least in part on the condition of the user, the controlled schedule, and a content of the notifications.

2. The computerized system of claim 1 wherein the scheduling component configures the controlled schedule between a plurality of administrators, users and presentation devices in at least one of a one to one, a one to many, a many to one and a many to many relationship, and wherein a multiple user settings configuration includes at least one of a family integrated calendaring, a diagnosis grouping, a grade level grouping, or an employee position grouping.

3. The computerized system of claim 1, wherein the user-familiar voice is a pre-recorded or rendered voice of the user.

4. The computerized system of claim 1, wherein the presentation device is operable to be controlled to display a plurality of panels as configured by the notification component and wherein each of the plurality of panels is controlled to display a plurality of content as configured by the scheduling component.

5. The computerized system of claim 4, wherein at least one of the plurality of panels is controlled to display a content that provides a combination of a user-familiar voice note and an image or video of user-familiar people.

6. The computerized system of claim 4, wherein the presentation device is operable to be associated with an input capability and the notification component comprises a monitoring component that receives the input from the presentation device.

7. The computerized system of claim 6, wherein the monitoring component receives inputs indicating queued event status as well as notifications having been completed by the user.

8. The computerized system of claim 4, wherein the notification component provides a notification flexibility on the presentation device comprising a mode of a plurality of panels; as well as a variable mode of panel placement and panel prominence, wherein the notifications are set by at least predetermined rules in the records module as integrated by the scheduling component.

9. The computerized system of claim 8, wherein notifications are based on at least an administrator choice, a user cognitive state, or a record in the record module, wherein information content and mode of notification is aligned with change in user cognitive state.

10. The computerized system of claim 1 further comprising an administrator device that is configured to be in communicative connection with the processor and that per a set of rules in the records module operates to edit, add, or delete the data and settings of administrator, user and presentation device in the records module.

11. The computerized system of claim 10, wherein the administrator device comprises a local set of records module, scheduling component and notification component, separated from the processor, and interacts directly with the presentation device through the local set.

12. An interactive computer-implemented automated method of remote scheduling that assists an end user through display panels on a presentation device associated with the end user, comprising:
- registering a combination of administrator, user and presentation device,
  - wherein registration includes or accesses a database of pertinent records, and
  - wherein pertinent records relate to administrative data and settings, user data and settings, and a presentation device data and settings;
- receiving inputs by a records module that coordinates, associates and tracks the administrator, user, presentation device data and settings, and interaction rules;
- integrating, by a scheduling component, records from the records module that include the data and settings of administrative, user and presentation device, and interaction rules, into a controlled schedule,
  - wherein the controlled schedule comprises presentation aspects of at least timing, duration, and actions taken when time passes and actions are completed; and
- providing, by a notification component, a set of queues and notifications to the presentation device, wherein the providing, by the notification component, comprises:
  - providing at least one of read only/display only notifications, static notifications, dynamic notifications, notifications rendered in text, visual, aural or combinations of text, visual and aural renderings,
    - wherein the notifications are associated with a condition of the user,
    - wherein the aural renderings are provided in at least one of a standard voice and a user-familiar voice,
      - wherein the user-familiar voice comprises pre-recorded notifications or notifications rendered in the user-familiar voice without being pre-recorded,
    - wherein the aural renderings comprise tonal qualities based at least in part on user conditions, the controlled schedule, and a content of the notifications; and
  - displaying on the presentation device, a plurality of panels as configured by the notification component and displaying a plurality of content as configured by the scheduling component,
    - wherein the display of content provides a combination of a user-familiar voice note and a subset of the plurality of panels provides an image or video of user-familiar people.

13. The method of claim 12, wherein the integrating, by a scheduling component, is performed in conjunction with a calendaring application.

14. A non-transitory computer readable storage medium comprising instructions that when executed by a processor perform a method, the method comprising:
- populating a records module with registration data, wherein registration data is associated with administrative data and settings, user data and settings, presentation device data and settings and interaction rules;
- coordinating, associating and tracking, by the records module, the administrator, user and presentation device data and interaction rules;
- integrating, by a scheduling component, records from the records module that include the data and settings of administrative, user and presentation device and interaction rules, into a controlled schedule,
  - wherein the controlled schedule comprises presentation aspects of at least timing, duration, and actions taken when time passes and actions are completed; and
- providing, by a notification component, a set of queues and notifications to the presentation device, wherein the providing comprises:
- providing further comprises:
  - providing at least one of read only/display only notifications, static notifications, dynamic notifications, notifications rendered in text, visual, aural or combinations of text, visual and aural renderings,
    - wherein the notifications are associated with a condition of the user,
    - wherein the aural renderings are provided in at least one of a standard voice and a user-familiar voice,
    - wherein the user-familiar voice comprises pre-recorded notifications or notifications rendered in the user-familiar voice without being pre-recorded,
    - wherein the aural renderings comprise tonal qualities based at least in part on user conditions, the controlled schedule, and a content of the notifications; and
- the method step of displaying further comprises:
  - displaying on the presentation device, a plurality of panels as configured by the notification component and displaying a plurality of content as configured by the scheduling component,
  - wherein the display of content provides a combination of user-familiar voice note and a subset of the plurality of panels provides an image or video of user-familiar people.

15. The non-transitory computer readable storage medium of claim 14, the method further comprising the steps of receiving inputs through a monitoring component and providing updated notifications through either a predetermined rule in the records module or through an on the fly command from an administrator device.

* * * * *